US 11,286,238 B2

(12) United States Patent
Li et al.

(10) Patent No.: US 11,286,238 B2
(45) Date of Patent: Mar. 29, 2022

(54) MELATONIN DERIVATIVES, METHOD THEREOF, AND USE THEREOF

(71) Applicants: Xiamen Nuokangde Biological Technology Co., Ltd., Fujian (CN); Yufei Li, Fujian (CN)

(72) Inventors: Yufei Li, Fujian (CN); Zhu Li, Fujian (CN); Yunpeng Tian, Fujian (CN); Jianghong Zhang, Fujian (CN); Qinbin Li, Fujian (CN); Xu Yan, Guangzhou (CN); Wanyun Li, Fujian (CN); Haiyang Wang, AnHui (CN); Ting Wu, Fujian (CN)

(73) Assignees: Yufei Li, Siming District (CN); Xiamen Nuokangde Biological Technology Co., Ltd., Xiamen (CN)

( * ) Notice: Subject to any disclaimer, the term of this patent is extended or adjusted under 35 U.S.C. 154(b) by 0 days.

(21) Appl. No.: 16/850,662

(22) Filed: Apr. 16, 2020

(65) Prior Publication Data

US 2021/0323917 A1    Oct. 21, 2021

(51) Int. Cl.
   *C07D 209/16*    (2006.01)
   *A61P 25/20*    (2006.01)
(52) U.S. Cl.
   CPC ............ *C07D 209/16* (2013.01); *A61P 25/20* (2018.01)
(58) Field of Classification Search
   CPC ............................... C07D 209/16; A61P 25/20
   USPC ........................................................ 514/419
   See application file for complete search history.

(56) References Cited

U.S. PATENT DOCUMENTS

2007/0197629 A1    8/2007    Somei et al.

FOREIGN PATENT DOCUMENTS

| CN | 109627202 A | 4/2019 |
| WO | 2014144725 A2 | 9/2014 |

OTHER PUBLICATIONS

Bhatia et al. A Review on Bioisosterism : A Rational Approach for Drug Design and Molecular Modification. (Year: 2011).*
"The Synthesis of Melatonin Antigens", 1979, Ian A. Blair and Christopher J. Seborn, Australian Journal of Chemistry, reprinted from the Internet at: https://www.publish.csiro.au/ch/CH9790399, pp. 399-403.

(Continued)

*Primary Examiner* — Timothy R Rozof
(74) *Attorney, Agent, or Firm* — Cooper Legal Group, LLC

(57) ABSTRACT

The present disclosure discloses melatonin derivatives, a method thereof, and a use thereof. The method comprises: dissolving melatonin in a solvent, adding a catalyst while maintaining the solvent at 0° C. to obtain a first reaction solution, stirring the first reaction solution, adding reactants in the first reaction solution, continually stirring at room temperature or at refluxing reaction temperature until, when analyzing by thin layer chromatography, the first reaction solution is fully reacted, quenching the reaction with ice water, concentrating the first reaction solution to obtain a residue of the first reaction solution, and purifying the residue of the first reaction solution by column chromatography to obtain the melatonin derivatives.

17 Claims, 4 Drawing Sheets

(56) References Cited

OTHER PUBLICATIONS

"Reduction of 1-pyrrolyl and 1-indolyl carbamates to hemiaminals", Dec. 2009, He-Chu Hsu and Duen-Ren Hou, Tetrahedron Letters, vol. 50, Issue 51, reprinted from the Internet at: https://www.sciencedirect.com/science/article/pii/S0040403909019704, 3 pgs.

"Macroscopic Wires from Fluorophore-Quencher Dyads with Long-Lived Blue Emission", Aug. 2017, Tao Wang, Ziye Wu, Wei Sun, Shengye Jin, Xingyuan Zhang, Chuanyao Zhou, Jun Jiang, Yi Luo and Guoqing Zhang, The Journal of Physical Chemistry, reprinted from the Internet at: https://pubs.acs.org/doi/10.1021/acs.jpca.7b08268, 8 pgs.

"Design and Synthesis of Sustain-Acting Melatonin Prodrugs", 2013, Pham Van Thoai and Nguyen Hai Nam, Journal of Chemistry, vol. 2013, Article ID 684760, reprinted from the Internet at: https://www.hindawi.com/journals/jchem/2013/684760/, 7 pgs.

"Antibodies to indolealkylamines II: site of conjugation of mealtonin to protein using formaldehyde", 1983, L.J. Grota, V. Snieckus, S.O. De Silva and G.M. Brown, Canadian Journal of Biochemistry and Cell Biology, reprinted from the Internet at: https://www.nrcresearchpress.com/doi/abs/10.1139/o83-139#.Xp9EkEnsY2w, 6 pgs.

"Synthesis of a New Water-Soluble Melatonin Derivative with Low Toxicity and a Strong Effect on Sleep Aid", Mar. 2020, Jianghong Zhang, Xu Yan, Yunpeng Tian, Wanyun Li, Haiyang Wang, Qinbin Li, Yufei Li, Zhu Li, and Ting Wu, ACS Omega, reprinted from the Internet at: https://www.ncbi.nlm.nih.gov/pubmed/32258885, 6 pgs.

\* cited by examiner

MELATONIN DERIVATIVES, METHOD THEREOF, AND USE THEREOF

RELATED APPLICATIONS

The instant application is related to Chinese Patent Application, 201811622426.5, filed on Dec. 28, 2018, which is incorporated herein by reference.

FIELD OF THE INVENTION

The present disclosure relates to the field of drug preparation and in particular relates to melatonin derivatives, a method thereof, and a use thereof.

BACKGROUND OF THE INVENTION

Melatonin (also known as N-acetyl-5-methichylamine) is an amine hormone produced by pineal glands of animals and humans and has a wide range of effects on the body. It can maintain the circadian rhythm, assist with sleep, enhance human immunity, assist with anti-aging, inhibit tumor growth, inhibit psychiatric diseases, provide vascular protection, and perform other functions. Melatonin is also an ancient pyridine plant hormone that plays an important role in plant growth regulation and resistance to harsh environments. Melatonin also has a powerful antioxidant function and can be used as a cosmetic skin care product. Studies have shown that melatonin is one of the least toxic substances, and human experiments have shown that taking up to a few grams a day for up to a month has almost no toxic side effects. Therefore, melatonin has attracted more and more attention from researchers. However, due to its molecular characteristics, its water solubility in water is extremely low, which greatly limits its medicinal efficacy. Due to its low water solubility, melatonin cannot be dissolved well in water during the preparation of drugs and plant growth regulators, and it can only be dissolved in organic solvents. Organic solvents increase the toxicity and side effects of melatonin. Moreover, due to the low water solubility of melatonin and its high fat solubility, it quickly penetrates the blood-brain barrier and stays in the blood in the brain for only a short period of time, affecting its efficacy. In studying the effects of melatonin on animals and humans, researchers also need to dissolve melatonin in water, which has limited its progress due to its low water solubility.

SUMMARY OF THE INVENTION

The present disclosure provides melatonin derivatives, a method thereof, and a use thereof to solve deficiencies of the existing techniques, greatly improving water solubility of melatonin.

The present disclosure provides melatonin derivatives having chemical structures as follows:

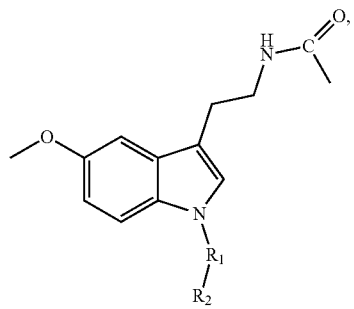

$R_1$ is $-(CH_2)_n-$ or $-CHO-(CH_2)_{n-1}-$, n=0-4.
$R_2$ is one selected from $-SO_3Na$, $-CO_2Na$, $-OH$, $-SO_3H$, or $-CO_2H$.

The present disclosure further provides a method for preparing melatonin derivatives having chemical structures as follows:

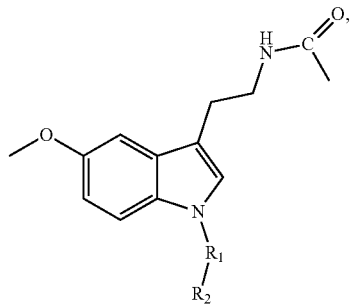

$R_1$ is $-(CH_2)_n-$ or $-CHO-(CH_2)_{n-1}-$, n=0-4.
$R_2$ is selected from $-SO_3Na$, $-CO_2Na$, $-OH$, $-SO_3H$, or $-CO_2H$.

The method comprises: dissolving melatonin in a solvent, adding a catalyst while maintaining the solvent at 0° C. to obtain a first reaction solution, stirring the first reaction solution, adding reactants in the first reaction solution, continually stirring at room temperature (e.g., 20-25° C.) or at refluxing reaction temperature (e.g., 50-80° C.) until, when analyzing by thin layer chromatography, the first reaction solution is fully reacted, quenching the reaction with ice water, concentrating the first reaction solution to obtain a residue of the first reaction solution, and purifying the residue of the first reaction solution by column chromatography to obtain the melatonin derivatives. The reactants are at least one selected from 1-4 butyrolactone, 1-3 propane sultone, sodium bromoethylsulfonate, sodium bromomethylsulfonate.

In a preferred embodiment, the solvent is at least one selected from tetrahydrofuran or acetonitrile.

In a preferred embodiment, the catalyst is at least one selected from sodium hydride or sodium carbonate.

The present disclosure further provides a method for preparing melatonin derivatives having chemical structures as follows:

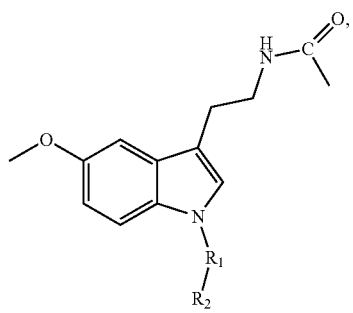

$R_1$ is $-(CH_2)_n-$ or $-CHO-(CH_2)_{n-1}-$, n=0-4.
$R_2$ is selected from $-SO_3Na$, $-CO_2Na$, $-OH$, $-SO_3H$, or $-CO_2H$.

The method comprises: dissolving melatonin in a solvent, adding a catalyst while maintaining the solvent at 0° C. to obtain a first reaction solution, stirring the first reaction solution, adding reactants in the first reaction solution, continually stirring at room temperature (e.g., 20-25° C.) or at refluxing reaction temperature (e.g., 50-80° C.) until, when analyzing by thin layer chromatography, the first reaction solution is fully reacted, quenching the reaction with ice water, concentrating the first reaction solution to obtain a residue of the first reaction solution, purifying the residue of the first reaction solution by column chromatography, adding alcohol and an alkali to the residue of the first reaction solution to obtain a second reaction solution, stirring the second reaction solution and reacting at room temperature (e.g., 20-25° C.), rotary evaporating the second reaction solution, and purifying a residue of the second reaction solution by the column chromatography to obtain the melatonin derivatives. The reactants is at least one selected from chlorosulfonic acid, ethyl bromoacetate, ethyl 3-bromopropionate, ethyl 4-bromobutyrate, ethyl 5-bromovalerate, glutaric anhydride, succinic anhydride, or ethyl malonyl chloride.

In a preferred embodiment, the solvent is at least one selected from dichloromethane or N,N-dimethylformamide.

In a preferred embodiment, the catalyst is at least one selected from 4-Dimethylaminopyridine or triethylamine.

The present disclosure further provides a use of the melatonin derivatives in a preparation of a sleep aid drug, an enhancing human immunity drug, an anti-aging drug, an anti-tumor drug, an anti-psychiatric disease drug, a vascular protection drug, or a plant growth promoter.

The present disclosure further provides a method, the method comprises: using the melatonin derivatives for treating a sleep deficiency, enhancing human immunity, treating aging, mitigating tumor growth, treating an anti-psychiatric disease, improving vascular protection, or improving plant growth.

Compared with existing techniques, the technical solution provided by the present disclosure has the following advantages.

The present disclosure provides for a melatonin derivative, prepared according to a method provided by the present disclosure, having water solubility that is nearly 700 times higher than that of melatonin, thereby avoiding toxicity and side effects caused by the use of organic solvents to dissolve melatonin during preparation of a drug.

Because the melatonin derivative is highly water-soluble, its fat solubility is low, thereby prolonging its residence time in the brain blood and increasing its efficacy. Researchers can easily dissolve the melatonin derivative in water for further research, which facilitates research work.

The melatonin derivative prepared by the present disclosure has almost the same physiological functions as melatonin (for example, treating a sleep deficiency, etc.) and can be applied to industries such as agriculture, cosmetics and medicine, and therefore has broad application prospects.

BRIEF DESCRIPTION OF THE DRAWINGS

The present disclosure is further described with the combination of the accompanying drawings together with the embodiments.

DETAILED DESCRIPTION OF THE EMBODIMENTS

Figure 1:
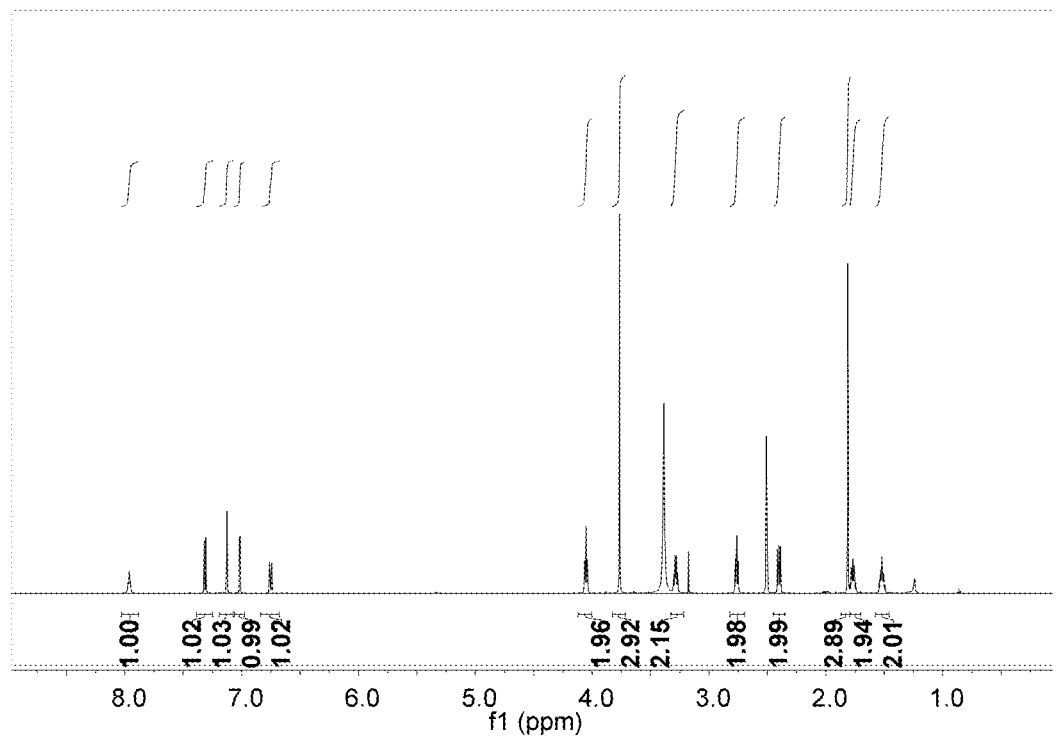
FIG. 1 illustrates a hydrogen nuclear magnetic resonance (NMR) spectrum of a melatonin derivative of Embodiment 1 of the present disclosure.

In a preferred embodiment, the reactants is at least one selected from 1-4 butyrolactone, 1-3 propane sultone, sodium bromoethylsulfonate, sodium bromomethylsulfonate, chlorosulfonic acid, ethyl bromoacetate, ethyl 3-bromopropionate, ethyl 4-bromobutyrate, ethyl 5-bromovalerate, glutaric anhydride, succinic anhydride, or ethyl malonyl chloride.

In a preferred embodiment, dissolving the melatonin in the solvent comprises dissolving 80-120 mg of the melatonin in 8-12 mL of the solvent, adding the catalyst comprises adding 60-137 mg of the catalyst in an ice bath, stirring the first reaction solution comprises stirring the first reaction solution for 25-35 minutes in the ice bath, adding the reactants comprises adding 79-136 mg of the reactants in the first reaction solution, continually stirring at room temperature or at refluxing reaction temperature comprises continually stirring the first reaction solution for 3-12 hours at the room temperature or the refluxing reaction temperature until, when analyzing by the thin layer chromatography, the first reaction solution is fully reacted, and quenching the reaction comprises adding 25-35 mL of the ice water to quench the reaction.

In a preferred embodiment, the alcohol comprises methanol and the alkali comprises sodium hydroxide.

In a preferred embodiment, an amount of the methanol is 8-12 mL, a concentration of the sodium hydroxide is 1.8-2.5 mol/L, and an amount of the sodium hydroxide is 2.8-5 mL.

The present disclosure further provides a melatonin derivative having a chemical structure as follows:

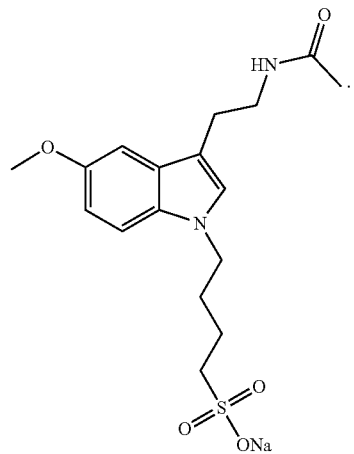

The present disclosure further provides a method for preparing the melatonin derivative, the method comprises: dissolving melatonin in tetrahydrofuran to obtain a solution, adding NaH into the solution in an ice bath to obtain a first reaction solution, stirring the first reaction solution, adding 1-4 butusult esters into the first reaction solution in the ice bath, continually stirring the first reaction solution at room temperature (e.g., 20-25° C.) until, when analyzing by thin layer chromatography, the first reaction solution is fully reacted, adding ice water to quench the reaction, concentrating the first reaction solution to obtain a residue of the first reaction solution, and purifying the residue of the first reaction solution by silica gel column chromatography to obtain the melatonin derivative.

In a preferred embodiment, dissolving melatonin in tetrahydrofuran comprises dissolving 80-120 mg of the melatonin in 8-12 mL of the tetrahydrofuran, adding the NaH into the solution comprises adding 60-80 mg of the NaH into the solution in the ice bath, stirring the first reaction solution comprises stirring the first reaction solution for 25-35 minutes in the ice bath, adding the 1-4 butusult esters comprises adding 80-95 mg of 1-4 butyrolactone into the first reaction solution, continually stirring the first reaction solution at the room temperature comprises stirring the first reaction solution for 3-12 hours until, when analyzing by the thin layer chromatography, the first reaction solution is fully reacted, and adding the ice water to quench the reaction comprises adding 25-35 mL of the ice water to quench the reaction.

The present disclosure is further described with the accompanying embodiments.

Embodiment 1

Figure 2:
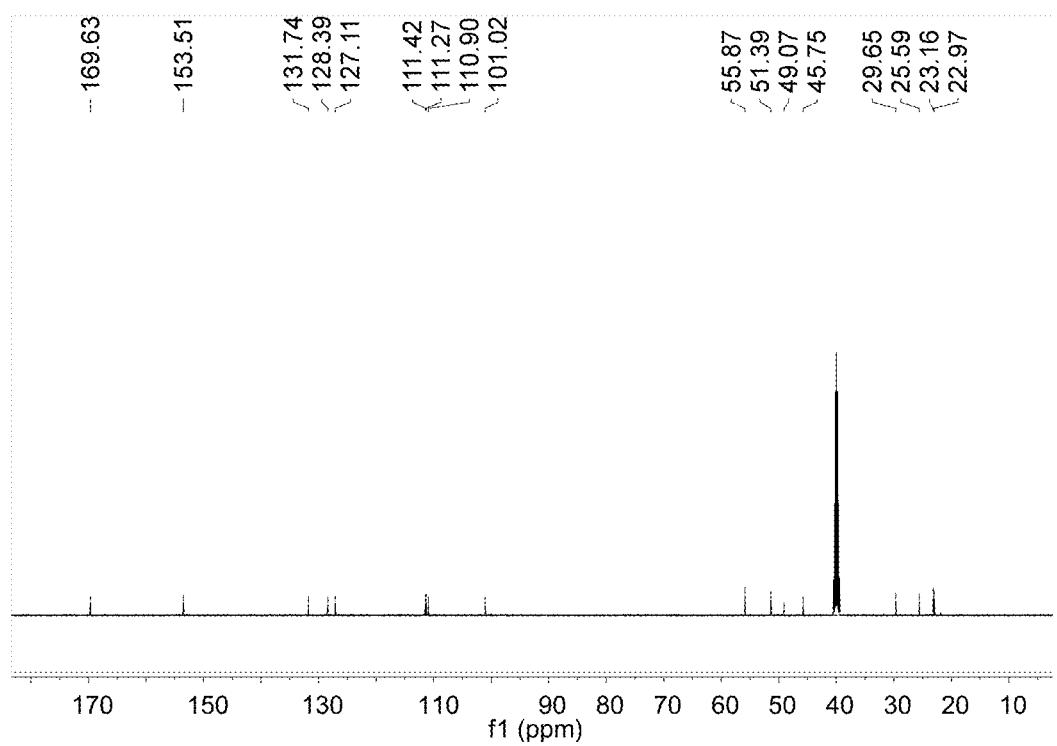
FIG. 2 illustrates a carbon NMR spectrum of the melatonin derivative of Embodiment 1 of the present disclosure.
Figure 3:
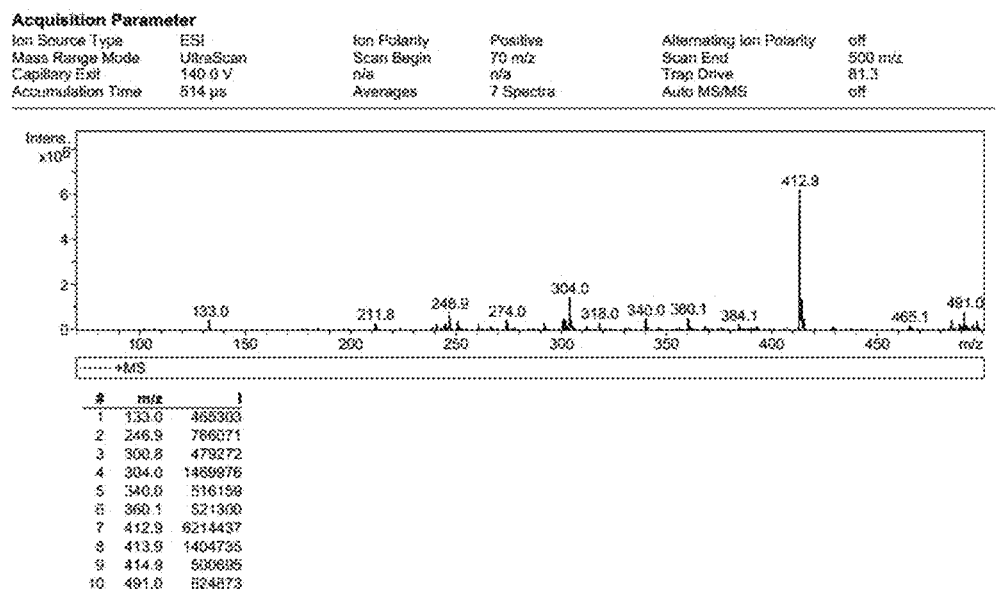
FIG. 3 illustrates a mass spectrum of the melatonin derivative of Embodiment 1 of the present disclosure.

Dissolving 100 mg melatonin (Mel) in 10 mL tetrahydrofuran (THF) to obtain a solution, adding 69 mg NaH in the solution in an ice bath to obtain a reaction solution, stirring the reaction solution and reacting for 30 minutes in the ice bath, dripping 88 mg 1,4-butane sultone into the reaction solution, then removing the ice bath and stirring the reaction solution overnight (e.g., 8-12 hours) at room temperature (e.g., 20-25° C.) until, when analyzing by thin layer chromatography, the reaction solution is fully reacted, adding 30 mL ice water to quench the reaction, then concentrating the reaction solution by a rotary evaporator in vacuum to obtain a residue of the reaction solution, and purifying the residue of the reaction solution by silica gel column chromatography to obtain 100 mg of a light yellow solid. A chemical structure of the light yellow solid is 4-(3-(2-acetamidoethyl)-5-methoxy-1H-indol-1-yl) butane-1-sulfonate (Mels, its yield is 59.5%). A hydrogen nuclear magnetic resonance (NMR) spectrum, a carbon NMR spectrum, and a mass spectrum of the light yellow solid is shown in FIGS. 1-3. A reaction route of the light yellow solid is as follows:

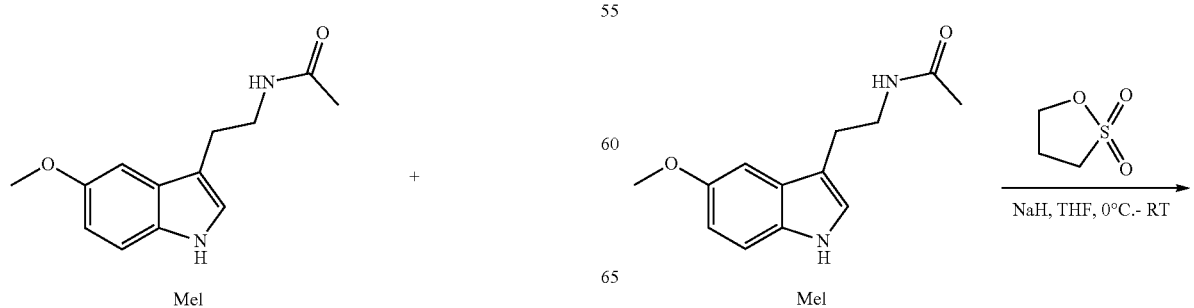

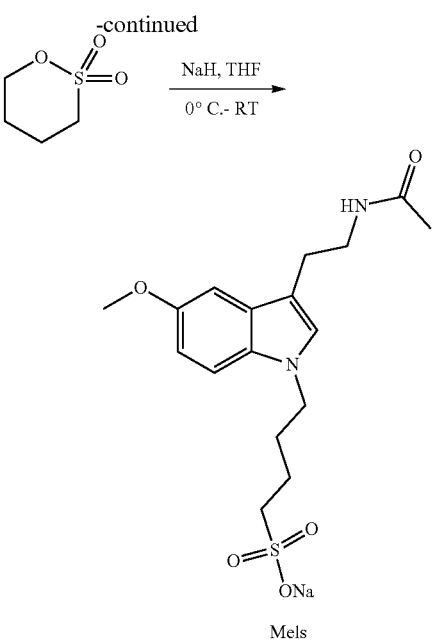

Mels

Analysis data of the light yellow solid is as follows:
$^1$H-NMR: (500 MHz, DMSO) δ 7.97 (t, J=5.6 Hz, 1H), 7.31 (d, J=8.8 Hz, 1H), 7.12 (s, 1H), 7.02 (d, J=2.4 Hz, 1H), 6.81-6.67 (m, 1H), 4.12-3.99 (m, 2H), 3.76 (s, 3H), 3.37-3.23 (m, 2H), 2.76 (t, J=7.4 Hz, 2H), 2.47-2.38 (m, 2H), 1.81 (s, 3H), 1.80-1.71 (m, 2H), 1.60-1.48 (m, 2H).
$^{13}$C-NMR: (126 MHz, DMSO) δ 169.63 (s), 153.51 (s), 131.74 (s), 128.39 (s), 127.11 (s), 111.42 (s), 111.27 (s), 110.90 (s), 101.02 (s), 55.87 (s), 51.39 (s), 49.07 (s), 45.75 (s), 29.65 (s), 25.59 (s), 23.16 (s), 22.97 (s).
ESI-MS m/z: [M+Na]+=412.9.

Embodiment 2

Dissolving 100 mg melatonin in 10 mL tetrahydrofuran (THF) to obtain a solution, adding 69 mg NaH into the solution in an ice bath to obtain a reaction solution, stirring the reaction solution for 30 minutes in the ice bath, dripping 79 mg 1,3-propane sultone into the reaction solution, then removing the ice bath and stirring the reaction solution overnight (e.g., 8-12 hours) at room temperature (e.g., 20-25° C.) until, when analyzing by thin layer chromatography, the reaction solution is fully reacted, adding 30 mL ice water to quench the reaction, then concentrating the reaction solution by a rotary evaporator in vacuum to obtain a residue of the reaction solution, and purifying the residue of the reaction solution by silica gel column chromatography to obtain a first product 1. A reaction route of the first product 1 is as follows:

-continued

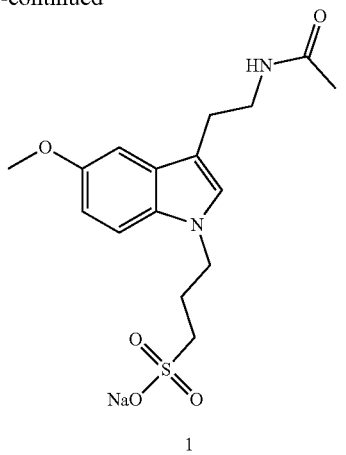

1

Embodiment 3

Dissolving 100 mg melatonin in 10 mL acetonitrile to obtain a solution, adding 137 mg sodium carbonate and 136 mg sodium bromoethylsulfonate into the solution to obtain a reaction solution, stirring the reaction solution overnight (e.g., 8-12 hours) at 80° C. until, when analyzing by thin layer chromatography, the reaction solution is fully reacted, concentrating the reaction solution in vacuum to obtain a residue of the reaction solution, and purifying the residue of the reaction solution by silica gel column chromatography to obtain a second product 2. A reaction route of the second product 2 is as follows:

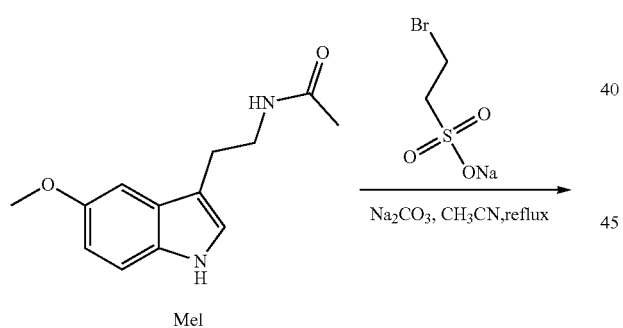

2

Embodiment 4

Dissolving 100 mg melatonin in 10 mL acetonitrile to obtain a solution, adding 137 mg sodium carbonate and 127 mg sodium bromomethylsulfonate into the solution to obtain a reaction solution, stirring the reaction solution overnight (e.g., 8-12 hours) at 80° C. until, when analyzing by thin layer chromatography, the reaction solution is fully reacted, concentrating the reaction solution in vacuum to obtain a residue of the reaction solution, and purifying the residue of the reaction solution by silica gel column chromatography to obtain a third product 3. A reaction route of the third product 3 is as follows:

3

Embodiment 5

Dissolving 100 mg melatonin in 10 mL dichloromethane to obtain a solution, adding 60 mg chlorosulfonic and 130 mg trimethamine into the solution to obtain a first reaction solution, stirring the first reaction solution for 3-5 hours at room temperature (e.g., 20-25° C.) until, when analyzing by thin layer chromatography, the first reaction solution is fully reacted, concentrating the first reaction solution in vacuum to obtain a residue of the first reaction solution, dissolving the residue of the first reaction solution with 10 mL methanol, then adding 3 mL sodium hydroxide solution with a concentration of 2M (2 mol/L), stirring for 30 min at room temperature (e.g., 20-25° C.) to obtain a second reaction solution, concentrating the second reaction solution in vacuum, and purifying a residue of the second reaction solution by silica gel column chromatography to obtain a fourth product 4. A reaction route of the fourth product 4 is as follows:

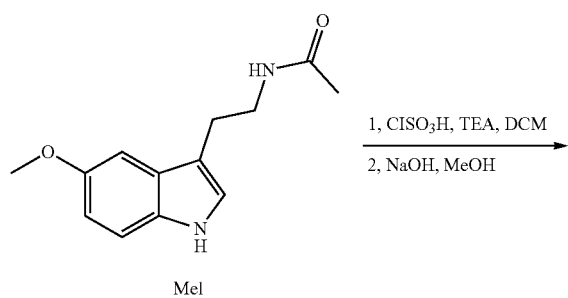
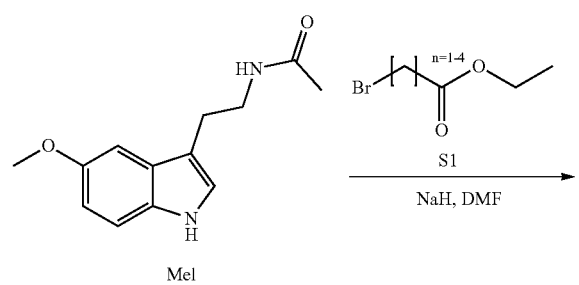
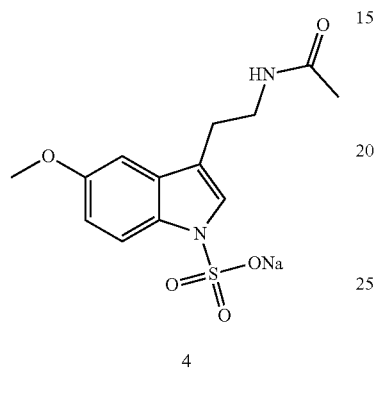
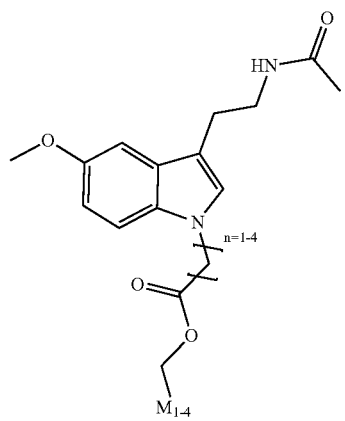
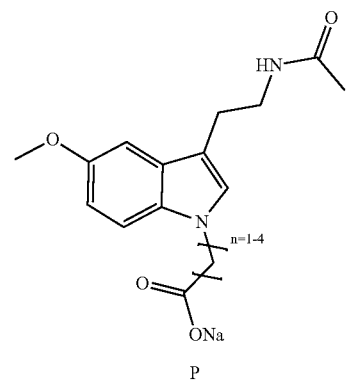

n=1, p=8
n=2, p=7
n=3, p=6
n=4, p=5

Embodiment 6

Dissolving melatonin (1 equivalent) in DMF (N,N-Dimethylformamide) to obtain a solution, adding NaH (3 equivalents) into the solution in an ice bath to obtain a first reaction solution, stirring the first reaction solution for 30 minutes in the ice bath, then separately adding ethyl bromoacetate, ethyl 3-bromopropionate, ethyl 4-bromobutyrate, or ethyl 5-bromovalerate (3 equivalents) into the first reaction solution to obtain a second reaction solution, removing the ice bath, stirring the second reaction solution overnight (e.g., 8-12 hours) at room temperature (e.g., 20-25° C.), concentrating the second reaction solution in vacuum, and purifying by silica gel column chromatography to respectively obtain a first intermediate product $M_1$, a second intermediate product $M_2$, a third intermediate product $M_3$, and a fourth intermediate product $M_4$, then separately dissolving each of the first intermediate product $M_1$, the second intermediate product $M_2$, the third intermediate product $M_3$, and the fourth intermediate product $M_4$ in a mixture solution of MeOH/H$_2$O (a volume ratio of MeOH/H$_2$O is 2/1), adding sodium hydroxide (2 equivalents) to obtain a third reaction solution, stirring the third reaction solution at room temperature (e.g., 20-25° C.) for 0.5 hours, concentrating the third reaction solution in vacuum, and purifying a residue of the third reaction solution by silica gel column chromatography to obtain a fifth product (p=5), a sixth product (p=6), a seventh product (p=7), and an eighth product (p=8), respectively corresponding to the first intermediate product $M_1$, the second intermediate product $M_2$, the third intermediate product $M_3$, and the fourth intermediate product $M_4$. Reaction routes of the fifth product (p=5), the sixth product (p=6), the seventh product (p=7), and the eighth product (p=8) are as follows:

Embodiment 7

Dissolving melatonin (1 equivalent) in dichloromethane (DCM) to obtain a solution, adding triethylamine (3 equivalents, TEA), glutaric anhydride or succinic anhydride (1.5 equivalents), and DMAP (4-dimethylaminopyridine, 0.1 equivalents) into the solution to obtain a first reaction solution, refluxing the first reaction solution overnight (e.g., 8-12 hours), then concentrating the first reaction solution to obtain a residue of the first reaction solution, dissolving the residue of the first reaction solution with methanol, adding sodium hydroxide (2 equivalents) with a concentration of 2M (2 mol/L) to obtain a second reaction solution, stirring for 30 minutes at room temperature (e.g., 20-25° C.), concentrating the second reaction solution in vacuum, and purifying a residue of the second reaction solution by silica gel column chromatography to obtain a ninth product 9 and a tenth product 10. Reaction routes of the ninth product 9 and the tenth product 10 are as follows:

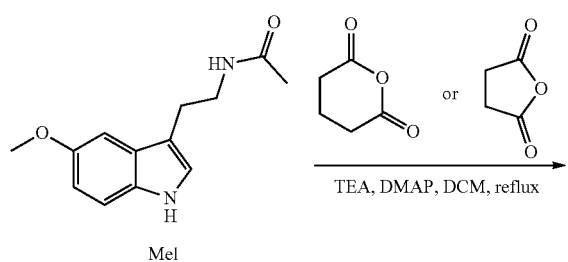

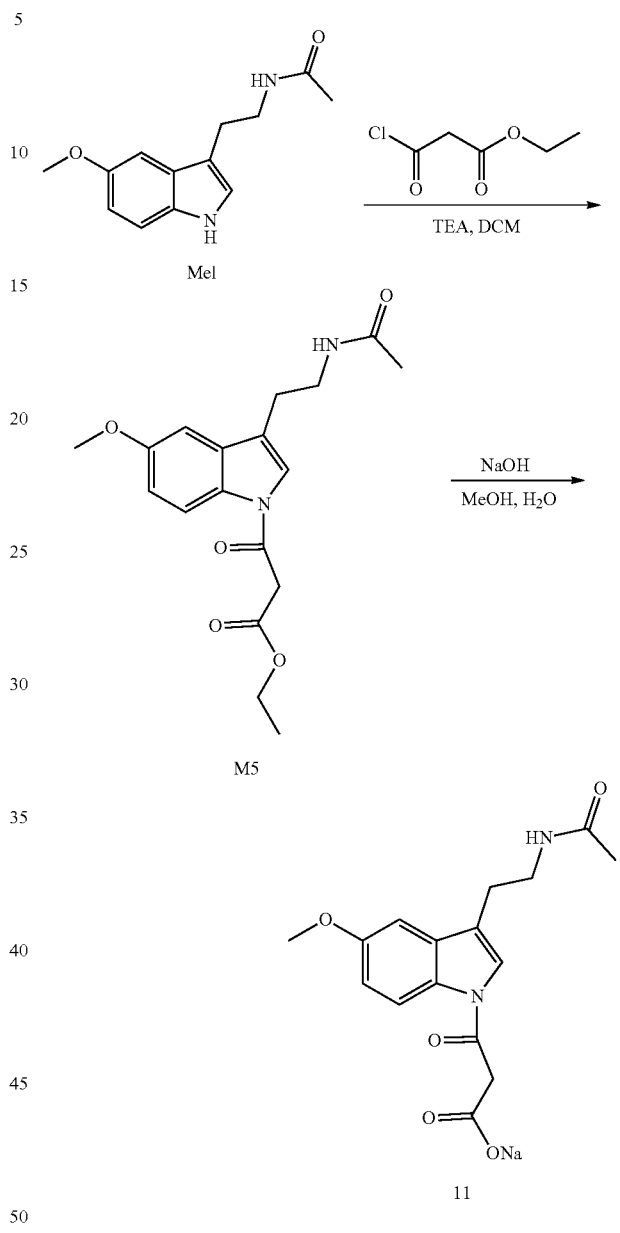

Embodiment 8

Dissolving melatonin (1 equivalent) in dichloromethane (DCM) to obtain a solution, adding triethylamine (3 equivalents, TEA) and then adding ethyl malonyl chloride (1.5 equivalents) into the solution to obtain a first reaction solution, stirring the first reaction solution at room temperature (e.g., 20-25° C.) for 5 hours, concentrating the first reaction solution, purifying by silica gel column chromatography to obtain an intermediate product $M_5$, dissolving the intermediate product $M_5$ in a mixture solution of MeOH/ $H_2O$ (a volume ratio of MeOH/$H_2O$ is 2/1), adding sodium hydroxide (2 equivalents) to obtain a second reaction solution, stirring the second reaction solution at room temperature (e.g., 20-25° C.) for 0.5 hours, concentrating the second reaction solution in vacuum to obtain a residue of the second reaction solution, and purifying the residue of the second reaction solution by silica gel column chromatography to obtain an eleventh product 11. A reaction route of the eleventh product 11 is as follows:

Embodiment 9

Dissolving the intermediate products $M_{1-2}$ (1 equivalent) obtained in Embodiment 6 in anhydrous tetrahydrofuran to obtain a solution, then adding $LiBH_4$ (3 equivalents) into the solution in an ice bath to obtain a reaction solution, stirring the reaction solution overnight (e.g., 8-12 hours) at room temperature (e.g., 20-25° C.) until, when analyzing by thin layer chromatography, the reaction solution is fully reacted. Extracting the reaction solution to obtain an organic phase of the reaction solution, concentrating the organic phase, and purifying a residue of the organic phase with silica gel column chromatography to obtain a thirteenth target molecule 13 and a twelfth target molecule 12. Reaction routes of the thirteenth target molecule 13 and the twelfth target molecule 12 are as follows:

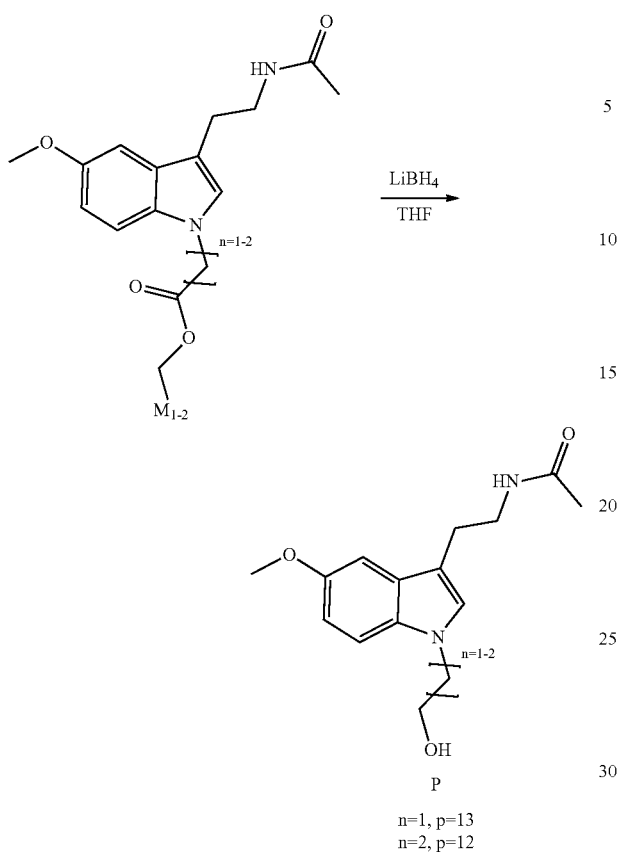

n=1, p=13
n=2, p=12

Embodiment 10: Solubility Determination

Figure 4:
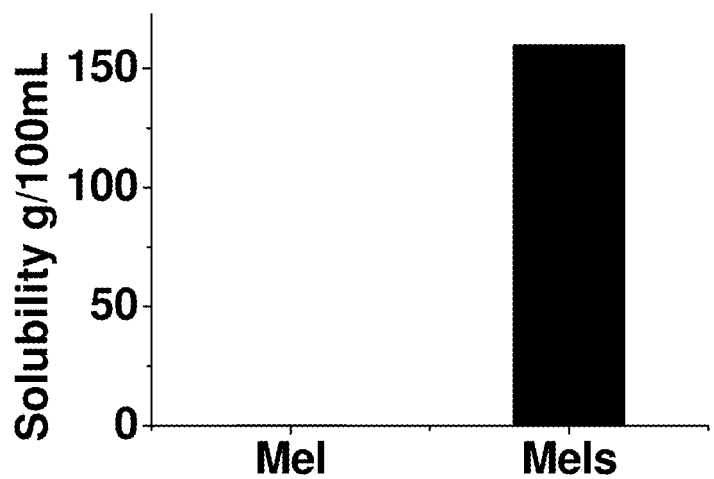
FIG. 4 illustrates a solubility experimental result of the melatonin derivative of Embodiment 1 of the present disclosure.

In order to evaluate solubility of a new melatonin derivative of Embodiment 1, solubility of Mel and Mels were tested. Solubility of Mels in 100 mL water is 160 g, while solubility of Mel in 100 mL water is 0.2 g, as disclosed in SCCS (Scientific Committee on Consumer Safety, Opinion on MLT, 23 Mar. 2010). Therefore, the solubility of Mels is nearly 700 times (695 times) the solubility of Mel (FIG. 4). Good water solubility of Mels can greatly improve application and greatly contribute to the research of this molecule in the field of medicine and biology.

Embodiment 11: Sleep Experiment

Figure 5:
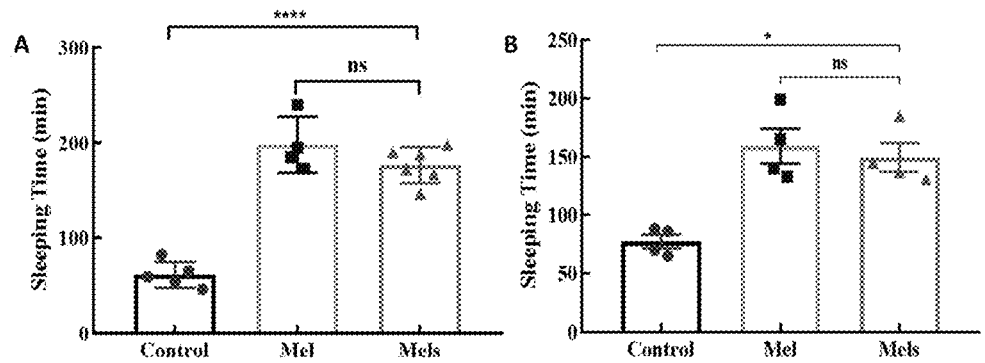
FIG. 5 illustrates a sleep experimental result of the melatonin derivative of Embodiment 1 of the present disclosure.

Mouse sleep models were established by injecting 300 μL 1% sodium pentobarbital solution into mice, and then dividing the mice into three groups. Each group comprised five mice. A first group of the three groups were injected with 100 μL normal saline as a control group, a second group of the three groups were injected with 100 μL natural unmodified melatonin (Mel) solution, a concentration of Mel was 86 μM (86 μmol/L) or 860 nM (860 nmol/L), and a third group of the three groups was injected with modified melatonin (Mels) solution with the same concentration and volume as that of the second group. A sleep duration began to be recorded one minute after a loss of righting reflex, and recording ended when the righting reflex returned. As shown in FIG. 5, the modified melatonin derivative Mels has the same effect as Mel, and it significantly prolonged a sleep time of mice from 1 hour to 3 hours.

Embodiment 12: Cytotoxicity Assays

Figure 6:
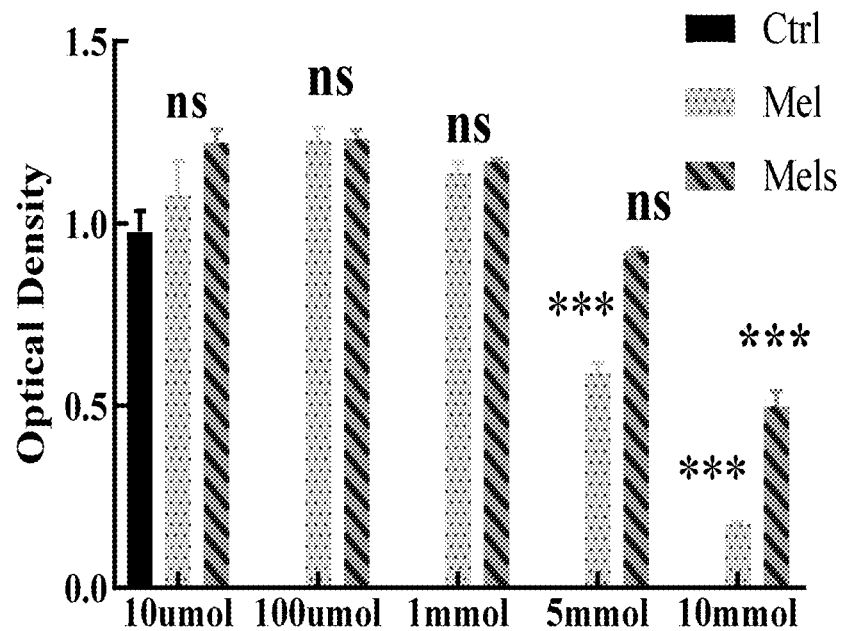
FIG. 6 illustrates a diagram of cell proliferation experimental effects of the melatonin derivative of Embodiment 1 with different concentrations.

B16F10 cell lines were incubated into a plate with 96 wells. After cell adherence, a Mel solution with different concentrations or a Mels solution with different concentrations was respectively added to one of the 96 wells in turn. Final concentrations of the Mel solution or the Mels solution were respectively 10 μM (10 μmol/L), 100 μM (100 μmol/L), 1 mM (1 mmol/L), 5 mM (5 mmol/L), and 10 mM (10 mmol/L). After incubating for 24 hours, CCK-8 (Cell Counting Kit-8) was added into each one of the 96 wells. Absorbance of the Mel solution and the Mels solution was measured at 450 nm. Results of the absorbance showed that Mel and Mels have no effects on cell proliferation at a low concentration (FIG. 6). At higher concentrations of 5 mM and 10 mM, Mel affected cell proliferation rate, while Mels had little affected on cell proliferation rate, which is significantly different from that of Mel. Even at an even higher concentration, the cytotoxicity of Mels on cells was much smaller than that of Mel.

Embodiment 13: Safety Verification In Vivo

Figure 7:
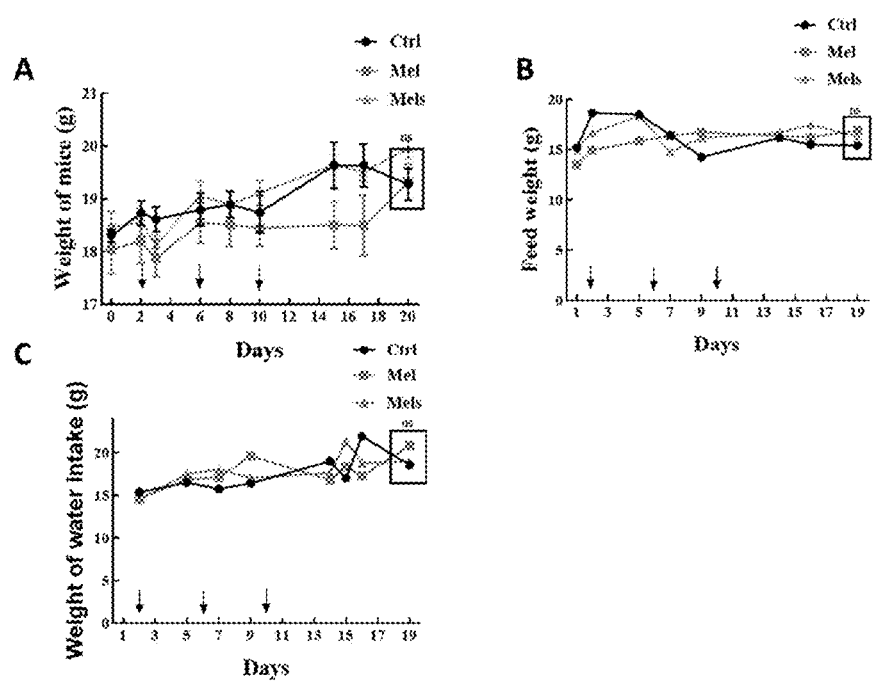
FIG. 7 illustrates results of mouse safety verification tests of the melatonin derivative of Embodiment 1 of the present disclosure.

To test a safety of Mels of Embodiment 1 in vivo, Mel, Mels, or saline was intraperitoneally injected into mice. Using C57/B6 mice (about 18 g), the mice were randomly divided into three groups: a control group, a Mel group, and a Mels group. Then, 200 μL of normal saline, Mel and Mels solution (dissolving Mel and Mels in saline containing 5% DMSO, 10 mmol/L) were respectively intraperitoneally injected into the mice. The injection process was repeated three times at days 2, 6, and 10, and body weight changes and diet changes of mice were recorded. As shown in FIG. 7, the injection of Mels had no significant effect on body weights and diets of the mice compared with the control group and the Mel group. Mels therefore had good safety in vivo. In short, Mels has lower toxicity and good safety in vitro and in vivo.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

What is claimed is:

1. Melatonin derivatives, wherein structures of the melatonin derivatives are as follows:

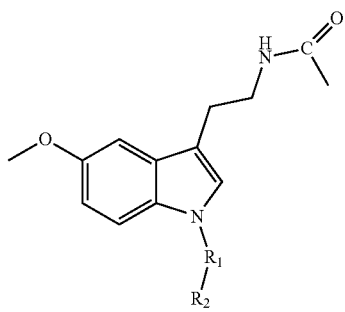

wherein: $R_1$ is $-(CH_2)_n-$ or $-C(O)-(CH_2)_{n-1}-$ and n=1-4, and $R_2$ is one selected from $-SO_3Na$, $-CO_2Na$, or $-SO_3H$, and when $R_2$ is $-CO_2Na$, $R_1$ is $-C(O)-(CH_2)_{n-1}-$.

2. A method for preparing the melatonin derivatives according to claim 1, wherein the method comprises:
dissolving melatonin in a solvent,
adding a catalyst while maintaining the solvent at 0° C. to obtain a first reaction solution,
stirring the first reaction solution,
adding reactants in the first reaction solution,
continually stirring at room temperature or at refluxing reaction temperature until, when analyzing by thin layer chromatography, the first reaction solution is fully reacted,
quenching the reaction with ice water,
concentrating the first reaction solution to obtain a residue of the first reaction solution, and
purifying the residue of the first reaction solution by column chromatography to obtain the melatonin derivatives,
wherein:
the reactants are at least one selected from 1-4 butyrolactone, 1-3 propane sultone, sodium bromoethylsulfonate, or sodium bromomethylsulfonate.

3. The method for preparing the melatonin derivatives according to claim 2, wherein the solvent is at least one selected from tetrahydrofuran or acetonitrile.

4. The method for preparing the melatonin derivatives according to claim 2, wherein the catalyst is at least one selected from sodium hydride or sodium carbonate.

5. A method for preparing the melatonin derivatives according to claim 1, wherein the method comprises:
dissolving melatonin in a solvent,
adding a catalyst while maintaining the solvent at 0° C. to obtain a first reaction solution,
stirring the first reaction solution,
adding reactants in the first reaction solution,
continually stirring at room temperature or at refluxing reaction temperature until, when analyzing by thin layer chromatography, the first reaction solution is fully reacted,
quenching the reaction with ice water,
concentrating the first reaction solution to obtain a residue of the first reaction solution,
purifying the residue of the first reaction solution by column chromatography,
adding alcohol and an alkali to the residue of the first reaction solution to obtain a second reaction solution,
stirring the second reaction solution and reacting at room temperature,
rotary evaporating the second reaction solution, and
purifying a residue of the second reaction solution by the column chromatography to obtain the melatonin derivatives,
wherein:
the reactants are at least one selected from chlorosulfonic acid, ethyl bromoacetate, ethyl 3-bromopropionate, ethyl 4-bromobutyrate, ethyl 5-bromovalerate, glutaric anhydride, succinic anhydride, or ethyl malonyl chloride,
the solvent is at least one selected from dichloromethane or N,N-dimethylformamide, and
the catalyst is at least one selected from triethylamine or 4-Dimethylaminopyridine.

6. The method for preparing the melatonin derivatives according to claim 2, wherein:
dissolving the melatonin in the solvent comprises dissolving 80-120 mg of the melatonin in 8-12 mL of the solvent,
adding the catalyst comprises adding 60-137 mg of the catalyst in an ice bath,
stirring the first reaction solution comprises stirring the first reaction solution for 25-35 minutes in the ice bath,
adding the reactants comprises adding 79-136 mg of the reactants in the first reaction solution,
continually stirring at the room temperature or at the refluxing reaction temperature comprises continually stirring the first reaction solution for 8-12 hours at the room temperature or at the refluxing reaction temperature until, when analyzing by the thin layer chromatography, the first reaction solution is fully reacted, and
quenching the reaction comprises adding 25-35 mL of the ice water to quench the reaction.

7. The method for preparing the melatonin derivatives according to claim 5, wherein:
dissolving the melatonin in the solvent comprises dissolving 80-120 mg of the melatonin in 8-12 mL of the solvent,
adding the catalyst comprises adding 60-80 mg of the catalyst in an ice bath,
stirring the first reaction solution comprises stirring the first reaction solution for 25-35 minutes in the ice bath,
adding the reactants comprises adding 80-95 mg of the reactants in the first reaction solution,
continually stirring at the room temperature or at the refluxing reaction temperature comprises continually stirring the first reaction solution for 8-12 hours at the room temperature or at the refluxing reaction temperature until, when analyzing by the thin layer chromatography, the first reaction solution is fully reacted, and
quenching the reaction comprises adding 25-35 mL of the ice water to quench the reaction.

8. The method for preparing the melatonin derivatives according to claim 5, wherein the alcohol comprises methanol and the alkali comprises sodium hydroxide.

9. The method for preparing the melatonin derivatives according to claim 8, wherein:
an amount of the methanol is 8-12 mL,
a concentration of the sodium hydroxide is 1.8-2.5 mol/L, and
an amount of the sodium hydroxide is 2.8-5 mL.

10. A melatonin derivative, wherein a structure of the melatonin derivative is as follows:

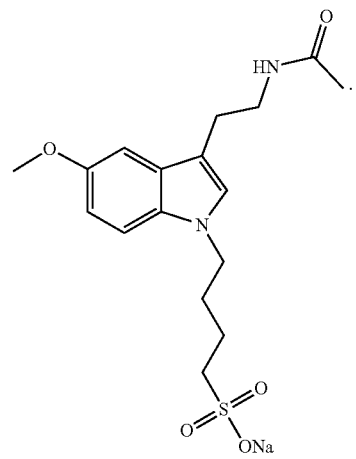

11. A method for preparing the melatonin derivative according to claim 10, the method comprising:
dissolving melatonin in tetrahydrofuran to obtain a solution,
adding NaH into the solution in an ice bath to obtain a first reaction solution,
stirring the first reaction solution,
adding 1-4 butusult esters into the first reaction solution in the ice bath,
continually stirring the first reaction solution at room temperature until, when analyzing by thin layer chromatography, the first reaction solution is fully reacted,
adding ice water to quench the reaction,
concentrating the first reaction solution to obtain a residue of the first reaction solution, and
purifying the residue of the first reaction solution by silica gel column chromatography to obtain the melatonin derivative.

12. The method for preparing the melatonin derivative according to claim 11, wherein:
dissolving the melatonin in the tetrahydrofuran comprises dissolving 80-120 mg of the melatonin in 8-12 mL of the tetrahydrofuran,
adding the NaH into the solution comprises adding 60-80 mg of the NaH into the solution in the ice bath,
stirring the first reaction solution comprises stirring the first reaction solution for 25-35 minutes in the ice bath,
adding the 1-4 butusult esters comprises adding 80-95 mg of 1-4 butyrolactone into the first reaction solution,
continually stirring the first reaction solution at the room temperature comprises stirring the first reaction solution for 8-12 hours until, when analyzing by the thin layer chromatography, the first reaction solution is fully reacted, and
adding the ice water to quench the reaction comprises adding 25-35 mL of the ice water to quench the reaction.

13. A method comprising:
using the melatonin derivatives of claim 1 for treating a sleep deficiency, enhancing human immunity, treating aging, mitigating tumor growth, treating an anti-psychiatric disease, improving vascular protection, or improving plant growth.

14. A method comprising:
using the melatonin derivative of claim 10 for treating a sleep deficiency, enhancing human immunity, treating aging, mitigating tumor growth, treating an anti-psychiatric disease, improving vascular protection, or improving plant growth.

15. The melatonin derivatives of claim 1, wherein $R_2$ is —$SO_3Na$.

16. The melatonin derivatives of claim 1, wherein $R_2$ is —$SO_3H$.

17. The melatonin derivatives of claim 1, wherein $R_2$ is —$CO_2Na$.

* * * * *